(12) United States Patent
Lander et al.

(10) Patent No.: US 9,849,086 B2
(45) Date of Patent: Dec. 26, 2017

(54) METHOD AND COMPOSITION FOR TREATING CYSTITIS

(71) Applicant: Nanologix Research, Inc., Rancho Mirage, CA (US)

(72) Inventors: Elliot B. Lander, Rancho Mirage, CA (US); Jackie R. See, Fullerton, CA (US)

(73) Assignee: Nanologix Research, Inc., Rancho Mirage, CA (US)

( * ) Notice: Subject to any disclaimer, the term of this patent is extended or adjusted under 35 U.S.C. 154(b) by 624 days.

(21) Appl. No.: 13/802,445

(22) Filed: Mar. 13, 2013

(65) Prior Publication Data

US 2013/0251785 A1 Sep. 26, 2013

Related U.S. Application Data

(60) Provisional application No. 61/612,515, filed on Mar. 19, 2012.

(51) Int. Cl.
| | |
|---|---|
| *A61K 9/127* | (2006.01) |
| *A61K 31/728* | (2006.01) |
| *A61K 31/726* | (2006.01) |
| *A61K 9/00* | (2006.01) |
| *A61K 31/727* | (2006.01) |

(52) U.S. Cl.
CPC ............ *A61K 9/127* (2013.01); *A61K 9/0034* (2013.01); *A61K 31/726* (2013.01); *A61K 31/727* (2013.01); *A61K 31/728* (2013.01)

(58) Field of Classification Search
CPC ............................... A61K 9/127; A61K 9/1271
USPC .......................................................... 424/450
See application file for complete search history.

(56) References Cited

U.S. PATENT DOCUMENTS

| | | | |
|---|---|---|---|
| 4,235,871 A | 11/1980 | Papahadjopoulos et al. | |
| 4,533,254 A | 8/1985 | Cook et al. | |
| 4,880,635 A | 11/1989 | Janoff et al. | |
| 2002/0012998 A1* | 1/2002 | Gonda et al. | 435/458 |
| 2005/0123593 A1* | 6/2005 | Thompson et al. | 424/450 |
| 2005/0234013 A1* | 10/2005 | Parsons | 514/54 |
| 2007/0122466 A1* | 5/2007 | Chancellor et al. | 424/450 |
| 2010/0104631 A1* | 4/2010 | Chancellor et al. | 424/450 |
| 2011/0318425 A1* | 12/2011 | Sandage et al. | 424/618 |
| 2012/0058969 A1* | 3/2012 | Riehl et al. | 514/54 |
| 2012/0321693 A1* | 12/2012 | Sullivan et al. | 424/450 |

OTHER PUBLICATIONS

Anderson, V.R. et al., "Pentosan Polysulfate: A Review of its Use in the Relief of Bladder Pain or Discomfort in Interstitial Cystitis", *Drugs*, 2006, vol. 66 (6) [abstract] (1 sheet).

(Continued)

*Primary Examiner* — Gollamudi Kishore
(74) *Attorney, Agent, or Firm* — Wilson Sonsini Goodrich & Rosati

(57) ABSTRACT

A medicament for treating cystitis and a method of treatment are provided. An agent to repair the damaged glycosaminoglycan ("GAG") layers lining the urothelium, noted in cystitis, such as pentosan polysulfate, hyaluronic acid, chondroitin, etc., is provided in a liposomal carrier. Cystitis is treated by intravesically administering to a patient a therapeutically effective dose of the medicament.

11 Claims, 2 Drawing Sheets

(56) References Cited

OTHER PUBLICATIONS

Chuang, Yao-Chi et al., "Intravesical Liposome Versus Oral Pentosan Polysulfate for Interstitial Cystitis/Painful Bladder Syndrome", *The Journal of Urology*, 2009, vol. 182, pp. 1393-1400.

Lee, W.C. et al., "Safety and Dose Flexibility Clinical Evaluation of Intravesical Liposome in Patients with Interstitial Cystitis or Painful Bladder Syndrome", *Kaohsiung J. Med. Sci.*, 2011, vol. 27 (10) [abstract] (1 sheet).

Tyagi, P. et al., "Bladder Instillation of Liposomes for Bladder Coating and Drug Delivery Platform", *LUTS*, 2009, vol. 1, pp. S90-S93.

Tyagi, P. et al., "Instillation of Liposomes vs Dimethyl Sulphoxide or Pentosan Polysulphate for Reducing Bladder Hyperactivity", *BJU Int.*, 2009, vol. 104 (11) [abstract] (1 sheet).

Chuang et al., Intravesical liposome versus oral pentosan polysulfate for interstitial cystitis/painful bladder syndrome. The Journal of Urology, 182:1393-1400, 2009.

Davis et al., Safety and efficacy of the use of intravesical and oral pentosan polysulfate sodium for interstitial cystitis: A randomized double-bind clinical trial. The Journal of Urology, 179:177-185, 2008.

Janicki et al., Intravesical liposome Drug Delivery and IC/BPS, Trans Anrdol Urol. 4(5): 572-578, 2015.

Lander and See. Intravesical pentosan polysulfate excapsulated in a liposome nanocarrier for interstital cystitis. Poster. Retrieved from: http://wsaua.org/2013/abstracts-essays/. 1 page, 2013.

Lee et al., Safety and dose flexibility clinical evaluation of intravesical liposome in patients with interstitial cystitis or painful bladder syndrome. Kaohsiung J Med Sci. 27(10):437-440, 2011.

Ratner, The Interstitial Cystitis Association of America; lessons learned over the past 30 years. Trans Anrdol Urol. 4(5):491-498, 2015.

Sant and Saban, Interstitial Cystitis/Bladder Pain Syndrome (IC/BPS) 2015: Part 1, Trans Anrdol Urol 4(5):484-485, 2015.

\* cited by examiner

METHOD AND COMPOSITION FOR TREATING CYSTITIS

CROSS-REFERENCE TO RELATED APPLICATION

The present application claims priority to and the benefit of U.S. Provisional Application Ser. No. 61/612,515 filed on Mar. 19, 2012, the entire content of which is incorporated herein by reference.

FIELD

The invention relates to methods of treatment and pharmaceutical compositions for treating various forms of cystitis, in particular the use of liposomal agents as nanocarriers for urothelial restorative therapy in cystitis.

BACKGROUND

Interstitial Cystitis (IC), also known as Interstitial Cystitis/Bladder Pain Syndrome (IC/PBS) is a chronic, severely debilitating, painful condition due to inflammation of the tissues of the bladder wall. The cause is unknown. Symptoms include pelvic pain and pressure, urinary frequency, burning and urgency, and painful intercourse.

IC/BPS is frequently misdiagnosed as a urinary tract infection. Patients often go years without a correct diagnosis. On average, there is about a 4-year delay between the time the first symptoms occur and the diagnosis is made. The condition is usually diagnosed by ruling out other conditions (such as sexually transmitted disease, bladder cancer, and bladder infections). Testing for IC/BPS is not always reliable. The KCl test, also known as the potassium sensitivity test, uses a mild potassium solution to test the integrity of the bladder wall.

The condition generally occurs around age 30 to 50, although it has been reported in younger people. Women are 10 times more likely to have IC/BPS than men. Studies reveal that as many as 3 to 8 million Americans suffer from IC/BPS. The condition is associated with depression, emotional trauma, and other syndromes such as fibromyalgia, endometriosis, and irritable bowel syndrome. Advanced cases may reveal ulcers and erosions in the bladder lining with ultimate scarring and shrinkage of the bladder.

The cause of IC/BPS is unknown. Theories have included neurologic, allergic, autoimmune, toxic exposure, genetic, abnormal mast cells, and psychological. It appears that most patients suffer from a deficiency of the protective glycosaminoglycan (GAG) layer of the inner bladder lining (urothelium). This results in increased permeability of the underlying submucosal tissues with subsequent tissue destruction.

Other forms of cystitis are also known, including hemorrhagic cystitis (including radiation- and chemical-induced cystitis), traumatic cystitis, and chronic cystitis caused by an infectious agent. In each case, the condition is associated with inflammation of the urothelial lining and loss of the glycosaminoglycan ("GAG") layer to some extent. This causes irritable voiding symptoms including pain, frequency, and urgency. Some of the most common forms of cystitis include:

Radiation Cystitis. This form of hemorrhagic cystitis can be disabling and potentially lethal. Radiation-induced degeneration and de-vascularization of the normal urothelium can occur even 10 years after ionizing radiation is delivered to the pelvis for the treatment of malignancy. Radiation cystitis can be treated with limited effectiveness and is usually incurable.

Chemical Cystitis. This form of hemorrhagic cystitis is often related to the administration of chemotherapy (cytoxan or ifosfamide). These agents can produce acrolein, which has an erosive effect on the urothelium and can cause significant irritative symptoms and even increase the risk for transitional cell carcinoma. Chemical cystitis can sometimes heal on its own.

Chronic Cystitis. Usually bacterial in origin (but can be viral), chronic cystitis is caused by infection. Bacterial infections make the bladder pre-disposed to recurrent infections and severe sensitivity with irritative symptoms. Symptoms can persist for some time even after the active infection is eradicated by appropriate antibiotic therapy.

There is no cure for interstitial cystitis, and there are no standard or consistently effective treatments. Treatment is currently based on trial and error and can include opioids, pain inhibitors, antidepressants, vistaril, detrussor relaxants, bladder hydrodistension, bladder instillations (in which a solution is introduced into the bladder via a catheter), biofeedback, dietary modification, and even surgery to enlarge or remove the bladder. Installations are intravesical treatments typically performed with a number of different combination "cocktails" that may include dimethyl sulfoxide (DMSO), steroids, heparin, chlorpactin, lidocaine, sodium hyaluronate (cystistat), chondroitin (uracyst), and sodium bicarbonate.

Elmiron® (pentosan polysulfate) is the only medication taken by mouth that is specifically approved for treating IC. There have also been reported attempts in the literature at intravesical instillation of Elmiron®. The KCl test has been determined to be helpful in predicting the success of Elmiron®.

Pentosan polysulfate (also known as sodium pentosan polysulfate and pentosan polysulfate sodium) is related to the low molecular weight heparin class of molecules. The official Elmiron® website (www.orthoelmiron.com) states that it is not known exactly how Elmiron® works. Preliminary clinical models suggest that the medicine coats the bladder and the pentosan polysulfate repairs damaged glycosaminoglycan (GAG) layers lining the urothelium. In vitro data suggest that it may provide an anti-inflammatory effect in patients with IC. Pentosan polysulfate shows beneficial effects in a proportion of patients with IC in terms of the improvement of a patient's overall condition and the relief of pain, and it is a generally well tolerated therapy. (Pentosan polysulfate: a review of its use in the relief of bladder pain or discomfort in interstitial cystitis. Anderson V R, Perry C M, Drugs. 2006; 66(6):821-35.) Although most controlled trials suggest a positive effect of oral Elmiron®, some studies have shown little benefit over placebo. It is the only U.S. FDA-approved oral treatment for the relief of bladder pain or discomfort associated with IC. The usual dose is 100 mg taken before or after meals three times per day. A veterinary version of Elmiron® is available under the trademark Cartrophen Vet®.

When administered orally, Elmiron® has pharmacokinetic limitations, as only 6% is absorbed and reaches the circulation, and a mean of 6% of an oral dose is excreted in the urine, mostly as desulfated and depolymerized metabolites. Only a small fraction of the administered dose (mean 0.14%) is recovered as intact drug in urine.

Oral Elmiron® is also associated with several systemic side effects, including hair loss, GI intolerance, headache, rash, sleep disturbance, and vertigo. Rarely, blood thinning can result.

Dr Lowell Parsons, who conducted the original studies on Elmiron®, has also studied intravesical Elmiron® instillation. According to the IC network, an online site that provides information about interstitial cystitis, several preliminary research studies that discussed new instillations were presented at the Bladder Symposium in October 2003, including: #1. Lowell Parsons presented the results for using Elmiron® intravesically. 40 patients were evaluated. 20 received heparin only (40,000 units of heparin) and 20 received Elmiron® (a solution of 100 mg oral Elmiron, 80 mg lidocaine and 3 cc's of sodium bicarb). 31 subjects had significant symptom relief. Nine had no change in their symptoms. In response to therapy, there was no significant difference between the two solutions. While heparin and Elmiron® had equal efficacy in the intravesical therapeutic solution, an advantage of pentosan polysulfate over heparin is its substantially lower cost.

There have been several reports in the literature describing the use of liposomes to coat the bladder. See, for example, Tyagi, P., et al., LUTS (2009) 1, S90-S93 (proposing that empty liposomes have a therapeutic effect by forming a coat on the injured urothelium and blocking irritation of submucosal afferent nerves); Lee, W. C., Kaohsiung J Med Sci 2011 Oct. 27 (10): 437-40 (reporting on the safety and dose flexibility clinical evaluation of liposomes in patients with IC, and documenting improvement in symptom scores and side effects); and Tyagi and Chancellor, BJU Int. 2009 December; 104(11):1689-92 (Epub 2009 Jul. 7) (comparing results in rats treated with instillation of liposomes versus intravesical pentosan polysulfate and versus intravesical DMSO. Intravesical liposomes had the most efficacy). Dr. Chancellor and the Lipella Company (www.lipella.com) have described the use of intravesical liposomes to carry the Botulinum toxin into the bladder wall.

Y C Chung et al. in J Urol 2009 October; 182(4):1393-400 reported on intravesical liposomes versus oral pentosan polysulfate for IC. They found intravesical liposomes achieved efficacy similar to that of oral pentosan polysulfate sodium, and concluded that intravesical liposomes appear to be a promising new treatment for interstitial cystitis/painful bladder syndrome. Some investigators have used empty liposomes to manage IC symptoms and found better results than with instillation of Elmiron® or DMSO. Tyagi P, Hsieh V C, Yoshimura N, Kaufman J, Chancellor M B, *"Instillation of liposomes vs dimethyl sulphoxide or pentosan polysulphate for reducing bladder hyperactivity,"* British Journal of Urology (BJU Int.) 2009 December; 104(11):1689-92. Epub 2009 Jul. 7. Y C Chung used empty liposomes and proved superior efficacy to oral Elmiron®. Chuang Y C, Lee W C, Lee W C, Chiang P H., J Urol. 2009 Aug. 13. Epub ahead of print. doi:10.1016/j.juro.2009.06.024.

Despite substantial efforts by the medical community to treat IC and other forms of cystitis, a truly effective treatment with few side effects has remained elusive.

SUMMARY

In a first aspect of the invention, a medicament for treating cystitis is provided and comprises a glycosaminoglycan ("GAG"), such as pentosan polysulfate, hyaluronic acid, chondroitin, etc., provided in a liposomal carrier. In a second aspect of the invention, cystitis is treated by intravesically administering to a patient a therapeutically effective dose of the medicament. While not bound by theory, it is believed that the new method of treating cystitis is urothelial restorative therapy, in which the inflammation and degeneration of the bladder urothelial lining is alleviated and the glycosaminoglycan layer of the bladder is restored.

BRIEF DESCRIPTION OF THE DRAWINGS

These and other features and advantages of the present invention will be better understood with reference to the following detailed description when considered in conjunction with the accompanying drawings wherein.

DETAILED DESCRIPTION

Figure 1:
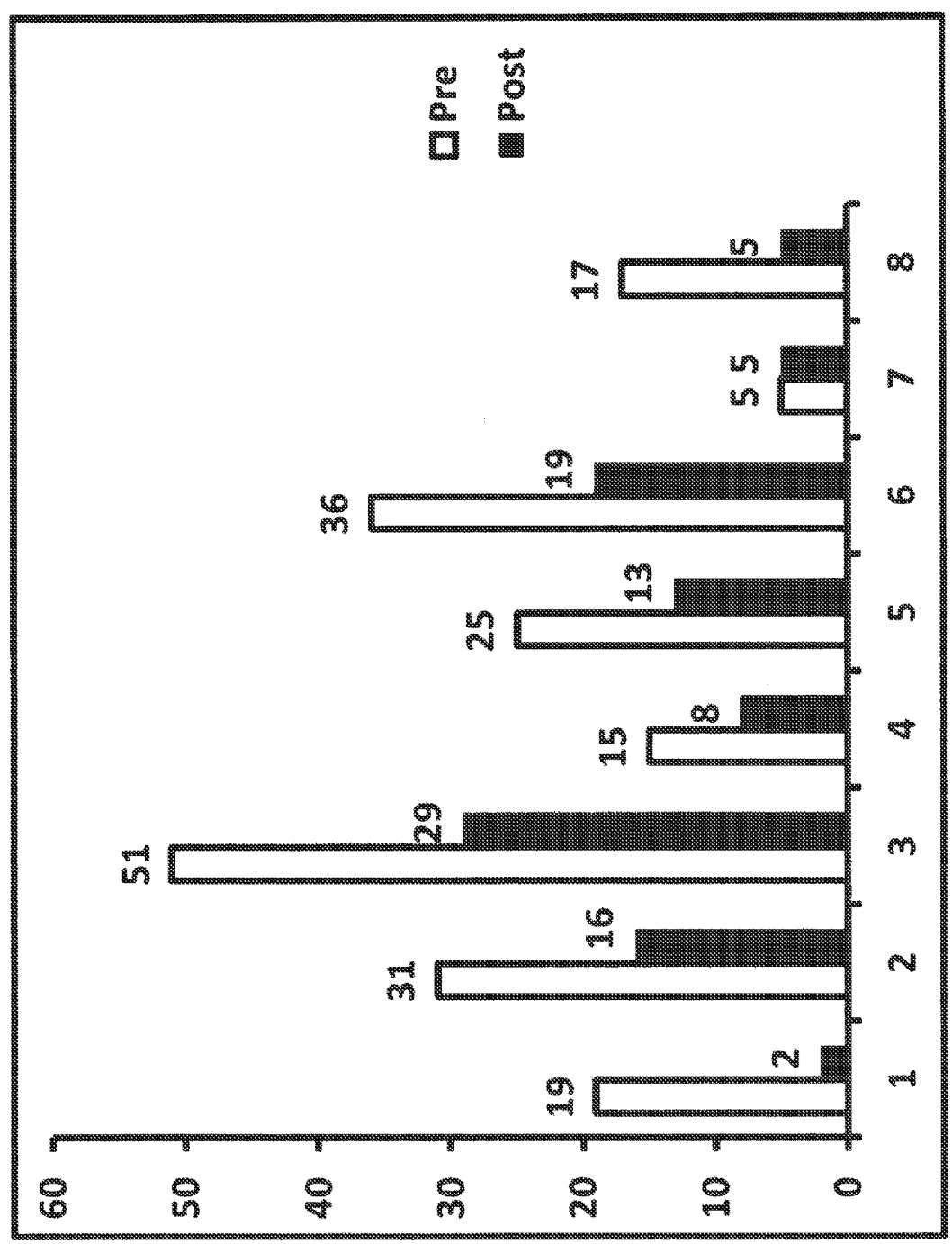
FIG. 1 is a bar graph showing pelvic urgency frequency (PUF) scores for eight patients treated using medicaments and methods according to embodiments of the present disclosure.

Aspects of embodiments of the present disclosure are directed toward improving drug delivery of a GAG, protecting a GAG molecule, prolonging dwell times of a GAG, and/or allowing for effective urothelial absorption of a GAG, to overcome drawbacks of current IC treatments such as inefficient oral absorption of GAGs and relatively rapid washout due to a hostile proton environment, which diminishes the efficacy of barrier restoration therapy.

In a first aspect of the invention, a medicament for treating cystitis is provided and comprises a glycosaminoglycan ("GAG") in a liposomal carrier. GAGs, also known as mucopolysaccharides, are long, unbranched polysaccharides consisting of a repeating disaccharide unit: a hexose or a hexuronic acid linked to a hexosamine. Both sulfated and unsulfated forms are known. Nonlimiting examples include chondroitins (e.g., chondroitin sulfate), dermatans (dermatan sulfate), heparans (heparan sulfate), heparins, hyaluronans (hyaluronic acid, hyaluronates), keratans (keratan sulfate), and pentosans (e.g., pentosan polysulfate). Also included are physiologically acceptable acid, base, ester, and salt forms of such compounds, and mixtures thereof. GAGs such as pentosan polysulfate, hyaluronic acid, chondroitin sulfate, and heparin are presently used to treat a number of medical conditions.

By "physiologically acceptable acid, base, ester, and salt forms of such compounds" is meant a GAG in its acid, base, salt, or ester form, provided that, in the case of a salt form, the counter ion is physiologically acceptable to a human, and, in the case of esters, the organic group R in the ester (~COOR) is a physiologically acceptable organic group. Esterification of one or more acid groups in a GAG molecule is accomplished using known organic chemistry techniques, e.g., reaction with an alcohol (ROH). An acid, base, and/or other catalyst can be employed to facilitate the reaction, so long as the disaccharide linkages are maintained.

By "liposomal carrier" is meant a collection or plurality of liposomes. The liposomes can be made of any physiologically suitable phospholipid, glycolipid, derived lipid, and the like. Nonlimiting examples of suitable phospholipids include phosphatidylcholine, phosphatidyl-serine, phosphatidic acid, phosphatidylglycerin, phosphatidylethanolamine, phosphatidyl-inositol, sphingomyelin, dicetyl phosphate, lysophosphatidyl choline, and mixtures of such lipids, such as soybean phospholipids and egg yolk phospholipids, e.g., lecithin. Suitable glycolipids include cerebroside, sulphurcontaining lipids, ganglioside, and the like. Suitable derived lipids include choleic acid, deoxycholic acid, and the like.

The liposomal carrier can be formed using any known method for forming liposomes, which can be loaded with a glycosaminoglycan using any known method for loading liposomes with a chemical agent. Water, 70% to 100% alcohol, and similar solvents can be used to dilute the liposome preparation. Known methods for forming liposomes containing chemical agents are described, for example, in U.S. Pat. No. 4,235,871 to Papahadjopoulos, et al., and Oral Microbiology and Immunology, 1994, 2: 146-153, 30 the disclosures of which are incorporated herein by reference.

In one embodiment, the liposomes have a mean diameter of less than 200 nm, preferably less than 80 nm, more preferably less than 50 nm, as determined by, e.g., negative staining electron microscopy. In one embodiment, for example, the liposomes have a mean diameter of about 50 to about 200 nanometers. Preparation of a substantially homogeneous population can be accomplished using conventional techniques, such as extrusion through a straight path or tortuous path-type filter Other methods of treating liposomes to form a homogenous size distribution include ultrasonic exposure (sonication), the French press technique, hydrodynamic shearing, homogenization using, for example, a colloid mill or Gaulin homogenizer, and microfluidization techniques. Microfluidization is a presently preferred method.

In one embodiment, pentosan polysulfate or other GAG in a homogeneous liposomal carrier is prepared by intermittent homogenizing at 16,000 rpm with a handheld immersion blender for approximately 2 minutes.

The liposomal carrier according to an embodiment may be homogenized with a suitable amount of the GAG. Any suitable amount of the liposomal carrier and the GAG may be used. For example, in one embodiment, an amount of the liposomal carrier ranges from about 100 mg to about 300 mg. In some embodiments, for example, the amount of the liposomal carrier ranges from about 100 mg to about 200 mg. In other embodiments, the amount of the liposomal carrier is about 150 mg, for example, in embodiments where the liposomal carrier is used with pentosan polysulfate (PP) as the GAG. In some embodiments, an amount of the GAG ranges from about 300 mg to about 600 mg. In some embodiments, for example, the amount of the GAG ranges from about 300 mg to about 500 mg. In other embodiments, the amount of the GAG is about 400 mg, for example, in embodiments where the GAG is pentosan polysulfate (PP). In some embodiments, a weight ratio of the liposomal carrier to the GAG is in a range of from about 1:6 to about 1:1. For example, in some embodiments the weight ratio of the liposomal carrier to the GAG is in a range of from about 1:5 to about 1:1. In another embodiment, the weight ratio of the liposomal carrier to the GAG is in a range of from about 1:5 to about 1:2. In another embodiment, the weight ratio of the liposomal carrier to the GAG is in a range of from about 1:3 to about 2:5. In another embodiment, the weight ratio of the liposomal carrier to the GAG is about 1.5:4, for example, in embodiments where the GAG is pentosan polysulfate (PP).

Microfluidization is described, for example, in U.S. Pat. No. 4,533,254 to Cook, et al., which is incorporated herein by reference. In one embodiment of a microfluidization procedure, the liposomal emulsion is forced at high pressure through a small diameter opening and splattered onto a wall and then collected. In sonication techniques, the raw materials for the liposomes, e.g., phospholipids, are combined with chemical agents, placed in a sonicator, and sonicated for a time, at a temperature and at a speed sufficient to obtain liposomes of the desired size.

The liposomes can be stored at reduced temperature, e.g., 40° F., until ready for use. In one embodiment, the liposomes, prior to administration, are treated to protect them against pH changes and micellization. In one embodiment, the liposomes are lyophilized. In another embodiment, the phospholipid (or any other constituent of the lipid wall) is treated with an additive, such as a crosslinking agent, prior to formation of the liposome.

Lyophilization may be accomplished by any method known in the art. Such procedures are disclosed, for example, in U.S. Pat. No. 4,880,836 to Janoff, et al., the disclosure of which is incorporated herein by reference. Lyophilization procedures can include the addition of a drying protectant to the liposome suspension to stabilize the liposome suspension so that the size and content of the liposomes are maintained during the drying procedure and through rehydration. Examples of drying agents include saccharide sugars, such as dextrose, sucrose, maltose, mannose, galactose, raffinose, trehalose lactose, and triose sugars, which can be added in amounts of about 5% to about 20%, more particularly, about 10%, by weight of the aqueous phase of the liposomal suspension. Manitol can be used in conjunction with any of the saccharides. Lyophilized liposomes can be reconstituted prior to use by adding water, saline, or other physiologically acceptable solvents.

The medicament as described herein may include one or more components in addition to the GAG and the liposomal carrier (e.g. additives and/or preservatives). For example, in some embodiments, the medicament further includes one or more components typically used in combination "cocktails" for treating IC, such as dimethyl sulfoxide (DMSO), steroids, heparin, chlorpactin, lidocaine, sodium hyaluronate (cystistat), chondroitin (uracyst), and/or sodium bicarbonate. In some embodiments, for example, the medicament further includes dimethyl sulfoxide (DMSO).

A preservative such as BHT, EDTA, urea, albumin, dextran, or polyvinyl alcohol can be added to individual packaged doses for office use. Packaging should emphasize sterility but may also be designed to allow easy homogenization through the opening of the package, which can fit tightly around the tip of a hand blender (having, e.g., a 2 inch diameter steel head) to allow homogenization inside the package prior to dispensing. In one embodiment, a convenient port allows aspiration with a piston "catheter tip" syringe for instillation. This can be part of a kit. In one embodiment, a kit contains liposomes, separately packaged GAG(s), and a syringe/catheter tip. The GAG(s) can be added to the liposomes and the resulting combination homogenized immediately prior to use, then loaded into the syringe for administration to a patient. Other ingredients, e.g., DMSO, can also be provided in the kit. DMSO has shown some effectiveness in treating IC.

In a second aspect of the invention, a method of treating cystitis is provided and comprises intravesically administering a therapeutically effective dose of a glycosaminoglycan ("GAG") in a liposomal carrier. As used herein, the term "intravesically" and similar terms refer to administration of a medicament into the bladder, e.g. by a catheter. The method can be used for glycosaminoglycan (GAG) barrier restoration.

GAGs suitable for use in the method of treating cystitis according to embodiments of the present disclosure include those already described above with reference to the medicament, including but not limited to chondroitins (e.g. chondroitin sulfate), dennatans (e.g. dermatan sulfate), heparans (e.g. heparan sulfate), heparins, hyaluronans (e.g. hyaluronic acid, hyaluronates), keratans (e.g. keratan sulfate), and pentosans (e.g. pentosan polysulfate), in addition to physiologically acceptable acid, base, ester, and salt forms of such compounds and mixtures thereof. In some embodiments, the glycosaminoglycan (GAG) is pentosan polysulfate (PP), which has been used safely both orally and intravesically for glycosaminoglycan (GAG) barrier restoration therapy, albeit somewhat ineffectively.

According to embodiments of the present invention, high quality multi-lamellar liposomes are used to encapsulate the GAG (e.g. pentosan polysulfate). In some embodiments, for example, the GAG is encapsulated according to a method suitable for encapsulating a GAG (e.g., according to the methods described herein, such as that described in Example 1).

In some embodiments, the GAG is encapsulated in a liposomal carrier, and the encapsulated GAG is administered to a patient with refractory interstitial cystitis. In some embodiments, the GAG is administered in a therapeutically effective dose. For example, in some embodiments, the therapeutically effective dose ranges from about 300 mg to about 600 mg of the GAG. In some embodiments, for example, the therapeutically effective dose ranges from about 300 mg to about 500 mg of the GAG. In another embodiment, the therapeutically effective dose is about 400 mg of the GAG, for example, in embodiments where the GAG is pentosan polysulfate (PP).

Upon instillation, patients are instructed to retain the compound at least 30 minutes if possible. During this retention period, patients are instructed to turn 90 degrees every 5 minutes with exam table reverse trendelenberg (tilted head down approximately 30 degrees) and with reverse trendelenberg (tilted head up approximately 30 degrees).

In some embodiments, the patient receives four or more administrations or instillations of the encapsulated GAG. The administrations or instillations may occur biweekly (i.e. every two weeks) such that a patient receives four administrations or instillations over a total period of six weeks, beginning with the first instillation. However, the instillations can occur over any suitable time frame.

In some embodiments, treating IC patients with medicaments according to the present disclosure and/or treating IC patients using methods according to the present disclosure, provide the patient with durable and/or sustained relief of the symptoms of IC. In some embodiments, for example, the durable and/or sustained relief of symptoms lasts for approximately 6 months or greater.

The following Examples are presented for illustrative purposes only and do not limit the scope of the invention.

Example 1. Preparation of a Medicament Containing a GAG in a Liposomal Carrier 1. 2,250 ml. of water (double distilled) is charged to a beaker (keep cool in ice bath, etc) and a nitrogen sparge is set for at least 30 minutes.
2. Add 225 grams of maltose (Sigma M5885) to the water and mix until dissolved. Keep the nitrogen sparge going. Maintain pH of 4.81 by adding acetic acid as needed.
3. In another beaker, 10.59 grams of egg phosphatidylcholine(EPC) (Sigma or equivalent substitute) is combined with 8.38 ml. of ethanol (anhydrous, Sigma E3884) and mixed until dissolved. To this add 67.5 mg. of BHT and mix until dissolved. To this mixture add 400 mg. of pentosan polysulfate, and mix until dissolved. Use the remaining 4.19 ml. of ethanol to rinse any remaining contents of the weighing container into the mixture.
4. Draw the ethanol solution into a 10 ml. syringe and add to the maltose solution over 11 minutes with continued nitrogen sparge. Keep pH<7.0 (goes into Microfluidizer at pH 4.81). Measure. Hand blade mixture. Keep everything cool at about 1.5 degrees C.
5. Add to Microfluidizer. Four passes through a M-110Y high-pressure pneumatic microfluidizer (Microfluidics, Newton, Mass.), with the pressure set at 16,000 psi. Keep the Microfluidizer homogenization chamber cooled (ice bath or other coolant) as the passage through the small aperture causes a microsecond of heating to occur.

| Ingredient | Quantity | Scale-up |
|---|---|---|
| EPC: | 10.59 g | 107.57 g |
| Maltose: | 225 g | 2,286 grams |
| Ethanol: | 12.57 ml | 127.69 ml. |
| BHT: | 67.5 mg | 685.7 ml |
| Pentosan polysulfate | 400 mg | 4,063 mg |
| (USP) Water: | 2,250 ml | 22,856 ml |

A multiplier of 10.158 is used for the scale-up.

The above protocol can be used to encapsulate up to about 2 grams (2,160 mg) of a GAG and one or more additional components.

Pentosan polysulfate can be obtained by opening capsules of Elmiron® and removing the contents. Each capsule contains 100 mg of pentosan polysulfate, and various excipients. The contents of four such capsules can be used to prepare a medicament containing 400 mg of pentosan polysulfate.

At 16,000 psi in the microfluidizer, localized heating can occur. The melting point of maltose is 102-103° C., so it is important to cool the mixing chamber using an ice bath or other cooling means.

Example 2. Instillation of GAG-Containing-Liposomes in an Interstitial Cystitis Patient 100 cc of liposomes containing pentosan polysulfate are placed in a 500 cc metal mixing bowel on a sterile field, and 100 cc of sterile water are slowly added as the mixture is homogenized over 1-2 minutes at 16000 rpm. The solution is then slowly instilled through a silicone catheter into a patient's bladder using a 70 cc piston syringe with a "catheter tip."

IC patients treated with an instillation containing Elmiron® in liposomes were able to retain the compound in their bladders for up to 45 minutes. In contrast, IC patients treated with standard intravesical instillations of "cocktails" containing one or more of heparin, bicarbonate, DMSO, lidocaine, etc., and no liposomes, could often tolerate the instillations for no more than 10 to 15 minutes. Preliminary studies on five patients treated with an Elmiron®-in-liposomes medicament showed no negative side effects. No infection, pain, bleeding, or system side effects were noted. All patients reported improvement in their symptoms as described in their Pelvic Urgency/Frequency scores and the O'Leary-Sant quality of life scores. Elmiron®-in-liposomes patients received 1 to 4 treatments separated by 2 weeks.

Example 3

Figure 2:
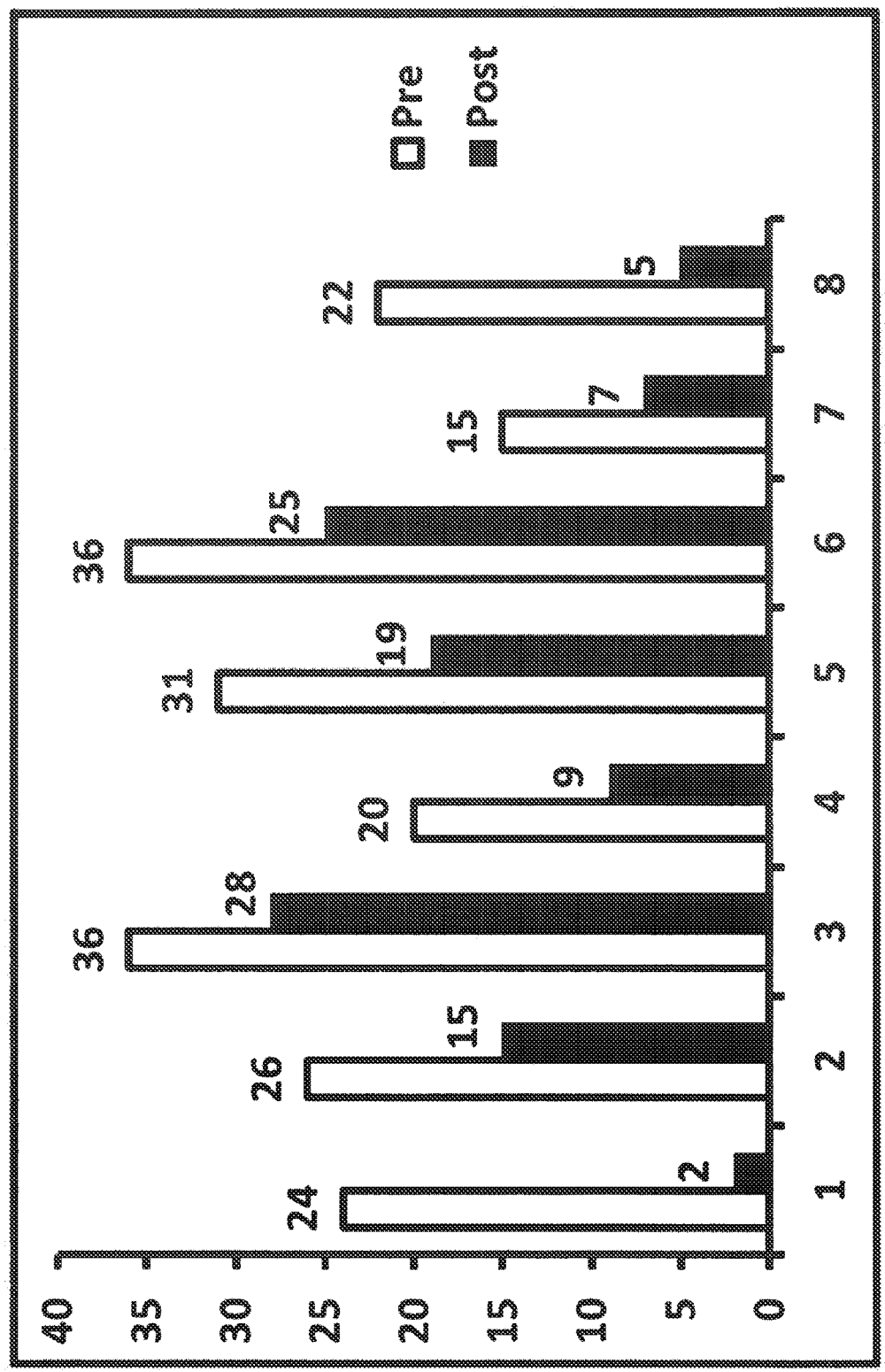
FIG. 2 is a bar graph showing O'Leary-Sant scores for eight patients treated using medicaments and methods according to embodiments of the present disclosure.

In this example, eight patients were confirmed to have refractory IC by NIDDK (National Institute of Diabetes and Digestive and Kidney Diseases) criteria, and were treated with four biweekly (i.e. every two weeks) intravesical instillations of 400 mg PP, which was homogenized at 16000 rpm with 150 mg of liposomes. The liposomes ranged from 50-200 nanometers in diameter. All of the patients had previously failed either oral and/or intravesical PP therapy. The mean number of treatments that the patients received was 4.6. Overall, the eight patients received a total of 37 treatments. Subjective outcome tools including O'Leary-Sant scores and Pelvic Urgency Frequency scores were used to evaluate efficacy of the treatment. The results of these evaluations are shown in FIG. 1 (Pelvic Urgency Frequency (PUF) scores) and FIG. 2 (O'Leary-Sant scores). In this example, no adverse events were recorded. Several of the patients noted durable and sustained relief of symptoms for greater than 6 months.

The O'Leary-Sant scores, as used in this example, can be used for evaluating whether a patient has IC or for evaluating patients with IC before, during, and/or after a treatment for IC. The O'Leary-Sant test scores include a symptom index and a problem index. The symptom index measures urgency and pain in patients being evaluated for IC. The problem index measures a degree to which patients experience each symptom. IC is typically diagnosed when a score of greater than 6 is provided in each symptom index.

The Pelvic Urgency Frequency scores, as used in this example, can also be used for evaluating whether a patient has IC or for evaluating patients with IC before, during, and/or after a treatment for IC. Additionally, Pelvic Urgency Frequency scores can be used for evaluating pelvic pain, and particularly, chronic pelvic pain in a patient. Pelvic Urgency Frequency scores focus on urgency and frequency issues in IC, and pain and symptoms associated with sexual intercourse. Here, a score of greater than 5 indicates approximately a 55% chance of IC, while a score of greater than 10 indicates approximately a 74% chance of IC.

As can be seen from this example, glycosaminoglycans (GAGs), and in particular, pentosan polysulfate (PP), are effective in mitigating the symptoms of IC when delivered intravesically to the urothelium in multi-lamellar liposomes.

From the preceding disclosure, various modifications and alternate embodiments of the invention will be apparent to persons skilled in the art to which the invention pertains. For example, one or more additional components can be included in the medicament. In one such embodiment, the medicament contains dimethyl sulfoxide in addition to the liposomes containing one or more GAG compounds. All such modifications and embodiments are within the scope of the invention, which is limited only by the appended claims and equivalents thereof.

What is claimed is:

1. A method of treating cystitis, comprising:
   intravesically administering a to a human a therapeutically effective dose of a pentosan in a liposomal carrier, wherein the weight ratio of the liposomal carrier to the pentosan is from about 1:3 to about 1:2.5.

2. A method as recited in claim 1, wherein the pentosan comprises pentosan polysulfate.

3. A method as recited in claim 1, further comprising hyaluronic acid or a physiologically acceptable ester or salt thereof.

4. A method as recited in claim 1, further comprising chondroitin sulfate.

5. A method as recited in claim 1, wherein the liposomal carrier comprises liposomes having a mean diameter of 50 nanometers or less.

6. A method as recited in claim 1, wherein the cystitis is interstitial cystitis, infectious cystitis, radiation cystitis, or chemical cystitis.

7. A method as recited in claim 1, wherein the cystitis is interstitial cystitis.

8. A method as recited in claim 1, wherein the cystitis is radiation cystitis.

9. A method as recited in claim 1, wherein the cystitis is chemical cystitis.

10. A method as recited in claim 1, further comprising co-administering DMSO with the pentosan in the liposomal carrier.

11. A method as recited in claim 1, wherein the therapeutically effective dose of the pentosan is between about 100 and about 600 milligrams of pentosan.

\* \* \* \* \*

UNITED STATES PATENT AND TRADEMARK OFFICE
CERTIFICATE OF CORRECTION

PATENT NO.      : 9,849,086 B2
APPLICATION NO. : 13/802445
DATED           : December 26, 2017
INVENTOR(S)     : Elliot B. Lander et al.

It is certified that error appears in the above-identified patent and that said Letters Patent is hereby corrected as shown below:

In Claim 1:
Column 10, Line 13, "intravesically administering a to a human a therapeuti-" should read
-- intravesically administering to a human a therapeuti- --

Signed and Sealed this
Eighth Day of May, 2018

Andrei Iancu
*Director of the United States Patent and Trademark Office*